(12) United States Patent
Farmer

(10) Patent No.: US 6,190,607 B1
(45) Date of Patent: *Feb. 20, 2001

(54) ROOM AIR FRESHENER

(76) Inventor: Mike Farmer, 4604 Deerfield Ct., Sioux Falls, SD (US) 57105

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/098,815

(22) Filed: Jun. 17, 1998

(51) Int. Cl.<sup>7</sup> ....................................................... A61L 9/00
(52) U.S. Cl. .................................. 422/5; 239/57; 239/60; 422/4; 422/120; 422/123
(58) Field of Search ................................... 422/4, 5, 120, 422/123, 306; 55/385.2, 385.3; 239/57, 60; D23/366, 368; 24/669, 702

(56) References Cited

U.S. PATENT DOCUMENTS

| | | |
|---|---|---|
| D. 281,102 | 10/1985 | Bush et al. . |
| D. 290,291 * | 6/1987 | Thompson ........................... D23/368 |
| D. 299,054 * | 12/1988 | Brun ..................................... D23/368 |
| D. 313,274 | 12/1990 | Peterson . |
| D. 346,856 * | 5/1994 | Kany ................................... D23/368 |
| D. 365,392 | 12/1995 | Van Gundy et al. . |
| D. 373,626 | 9/1996 | Dente et al. . |
| D. 382,050 * | 8/1997 | Hayes ................................... D23/368 |
| D. 417,727 | 12/1999 | Christianson . |
| 766,500 * | 8/1904 | Hatfield ..................................... 24/669 |
| 1,519,380 * | 12/1924 | Kochanski ............................. 24/669 |
| 2,560,681 | 7/1951 | Berkwoitz . |
| 2,721,098 | 10/1955 | Mangels . |
| 2,806,315 | 9/1957 | Kalensky . |
| 3,185,394 | 5/1965 | Farrell . |
| 3,733,016 | 5/1973 | Rood . |
| 4,432,938 | 2/1984 | Meetze, Jr. . |
| 4,523,870 | 6/1985 | Spector . |
| 4,802,626 | 2/1989 | Forbes et al. . |
| 4,808,347 | 2/1989 | Dawn . |
| 4,813,344 | 3/1989 | Greif . |
| 4,892,711 | 1/1990 | Tendick, Sr. ......................... 422/125 |
| 4,903,584 | 2/1990 | Styles . |
| 5,240,653 * | 8/1993 | Ramkissoon ......................... 422/123 |
| 5,269,723 | 12/1993 | Bander . |
| 5,273,690 * | 12/1993 | McDowell ............................ 422/124 |
| 5,368,822 | 11/1994 | McNeil . |
| 5,383,765 * | 1/1995 | Baxter et al. ......................... 422/124 |
| 5,407,642 * | 4/1995 | Lord ..................................... 422/120 |
| 5,422,078 * | 6/1995 | Colon ................................... 422/123 |
| 5,478,505 * | 12/1995 | McElfresh et al. .................. 422/124 |
| 5,527,493 | 6/1996 | McElfresh et al. .................... 261/30 |
| 5,547,636 * | 8/1996 | Vick et al. ............................ 422/124 |
| 5,603,455 | 2/1997 | Lin . |
| 5,762,549 | 6/1998 | Scheuer et al. . |
| 5,772,959 * | 6/1998 | Bermas ................................. 422/120 |
| 5,775,876 | 7/1998 | Walker et al. . |
| 5,820,791 * | 10/1998 | Canale .................................. 422/124 |
| 5,833,929 | 11/1998 | Watson et al. . |
| 5,932,147 | 8/1999 | Chen . |

* cited by examiner

*Primary Examiner*—Krisanne Thornton
(74) *Attorney, Agent, or Firm*—Fulwider Patton Lee & Utecht, LLP

(57) ABSTRACT

A room air freshener adapted to be used in connection with a register vent. The structure of the freshener is especially formed to be attached to the vent register and includes a formed handle adapted to keep the freshener material adjacent to the grid of the register vent. A certain range in the amount of mass of the freshener is required for a certain volume of air for best operation of the freshener.

25 Claims, 1 Drawing Sheet

ROOM AIR FRESHENER

BACKGROUND AND SUMMARY OF THE INVENTION

This invention pertains to air fresheners such as may be used in rooms required to be heated or cooled for living or working. It is related to the device described in applicant's co-pending application, Ser. No. 08/857,518 filed May 16, 1997 for an air freshener for use in automobiles. In contrast to that device, the present invention includes specific forms for attachment to vents used to vent air from building furnaces or air conditioners into room areas.

Unpleasant odors are frequent in many rooms in houses and places of work. Typical of such rooms would be restrooms, bathrooms, rooms designed for entrance into farm houses from livestock units, rooms specifically designated for use by tobacco smokers, etc. The distress caused by such odors can be alleviated by use of various types of air fresheners including such as may be hanging in the air in the room or which can be placed in receptacles.

By the present invention, the freshener material can be introduced into the room by being carried in the air from an air conditioner or a forced air type furnace. The air freshening material is carried on a clip which is readily fastened into the usual type of outlet vent register for such a unit, and this assures that the air freshening material is properly spread throughout the room. The clip is designed to hold itself in place on the register.

It is also necessary that the clip be designed to provide a proper relationship between the mass of the clip and the volume of air passing through the clip. The clip is designed to provide for such proper relation.

DESCRIPTION

Figure 1:
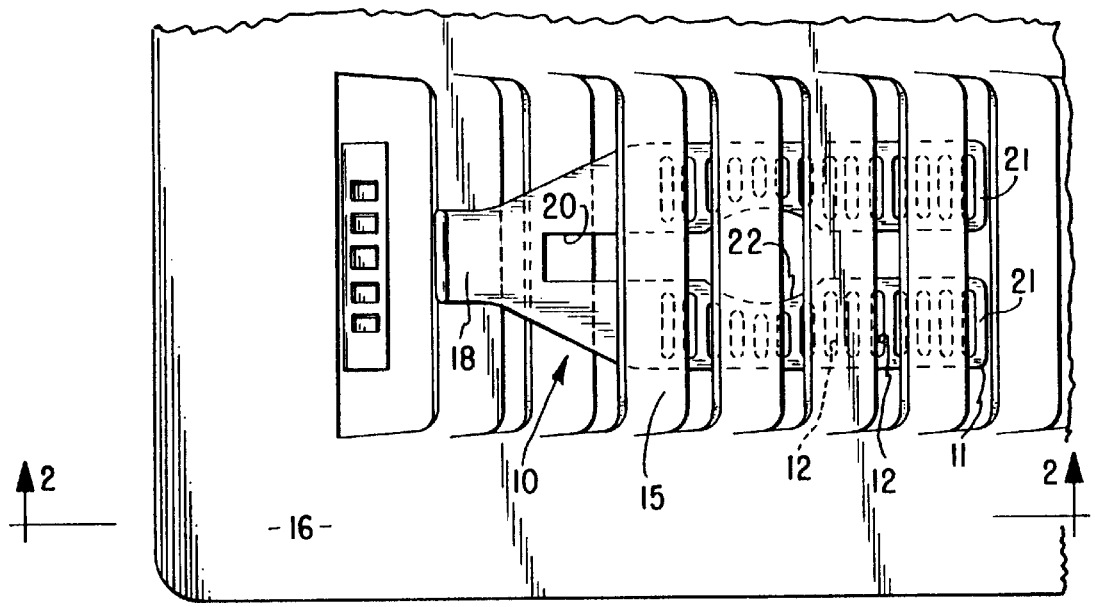
FIG. 1 is a partial top plan view of a register with a clip in place.
Figure 2:
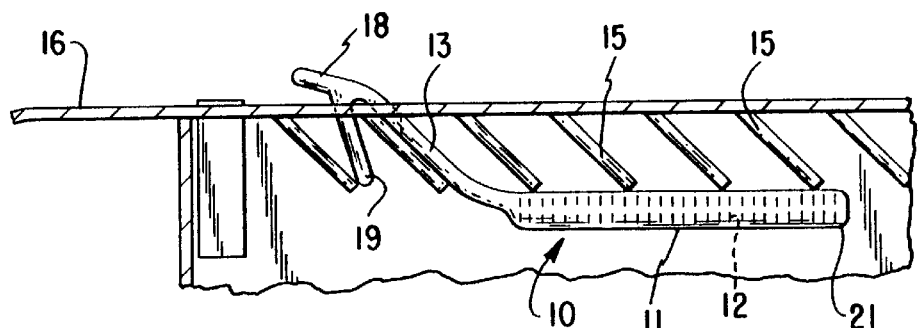
FIG. 2 is a sectional view from line 2—2 of FIG. 1.
Figure 3:
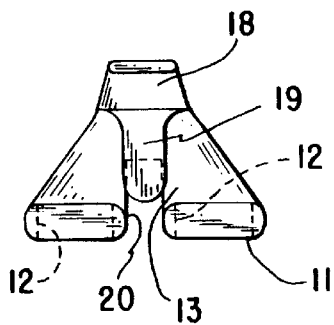
FIG. 3 is an end view of the clip removed from the register.

Briefly this invention comprises a clip which can be impregnated with an air freshening or scented material. The clip is formed to be held in place by its form alone in a heating or cooling air vent and to maintain its position in the vent.

More specifically and referring to the figures, the clip 10 is formed of a polymer which is preferably impregnated with a scented material. The clip is designed to be held in a vent register 16 of a type customarily used in a home heating and air conditioning system using forced air as a medium by which to heat or cool. The device is designed to be used in such a vent whether the vent is in the floor, ceiling or side walls.

The clip is preferably made of a polymer of a type which can be, and often is, impregnated with a scented material. This material is the same type as used for the automobile freshener described in the co-pending application noted above. Thus the material of the clip is relatively stiff but not rigid, having enough resilience to be bent slightly and to snap back into position.

The clip is formed as a flat or planar perforated sheet 11 which is perforated by slots 12. This sheet is designed to lie perpendicular to the direction of the air flow so that the air will go through the slots 12 to pick up the scented material impregnated into the sheet 11. The number and size of the slots may be varied so as to provide for the optimum usefulness. For example, if the scented material is used too quickly, the number or size of the slots can be diminished to reduce the air flow and to add to the material available to absorb the scent. From experiments, it has been discovered that the apparent best results are achieved by use of a 15% to 25% fragrance load. That is the weight of the fragrance material is approximately 20% of the total weight of the device. For example a very satisfactory result is obtained by using an area of 8.6 square inches of surface of a ⅛ inch thick sheet and 5.8 grams of fragrance equalling about 1.48 square inches per gram of fragrance. This calculates to a 20% fragrance load and is found satisfactory.

In order to hold the sheet 11 in place and to allow easy insertion, a handle may be used. This handle includes a sloped portion defining a transition neck 13 sloping from the sheet 11 at an obtuse angle of approximately 120 degrees. That is a common slope of the louvers 15 relative to the surface of the vent register 16 so that the sloped portion 13 of the handle will lie just against a louver after insertion.

A handle 18 extends from the sloped portion to form a finger grasp free extremity to provide for ease of insertion of the device into the register. A tongue 19 extends downwardly from the finger grasp portion of the handle 18 to project between two louvers 15 to hold the device in place. This tongue 19 should be long enough to extend from the top or outside of one louver to reach the adjacent louver to provide for relatively firm attachment to the register 16. It should be noted that the polypropelene material of which the clip is made is fairly stiff but not rigid so that there is a modest amount of flexibility in the material which the clip is being inserted.

To insert the clip 10 into the register it is necessary that the device can avoid interference with the control vane present in most registers which controls the overall flow of air. This is done simply by forming the clip with a central slot 20 extending from the free end 21 of the clip towards the handle end. Thus, the clip is of bifurcated form having a pair of legs adapted to straddle the central vane in the register as the clip is being inserted. Midway of the slot 20, a cut out may be formed to define an opening 22 to provide for a use to be described hereinafter.

To insert the clip, then, the legs are inserted between the louvers and straddling the control vane. The process of insertion is continued until the sloping neck part 13 of the handle reaches the louvers 15. At that time, the clip will be tilted relative to the register 16 as the clip is further inserted until the tongue 17 can be inserted between a pair of adjacent louvers 15. At that time the clip should be in a working plane contact with the tips of the louvers opposite the outer surface of the register 16. The handle can then be pressed into a place so that the tongue 19 extends to the adjacent louver to hold the entire clip in place. When this point is reached, the clip is again free of the control vane of the register so that the slot 20 is no longer of great consequence except as it relates to the amount of space through which the air passes.

It should also be noted that by the formation of the handle having the sloped portion 13, the use of the device in a ceiling register is made easy. After insertion, the body of the freshener will simply lie against the louvers which form the slots in the register, and when removal becomes desirable, that removal is made easy by the shape of the handle.

The opening 22 provides an expedient by which the clip may be adapted to an alternative use on a ceiling fan. It will be readily apparent that the clip can be used on the stem of such a fan simply by spreading the legs 21 to open the slot slightly and to straddle the stem. As the clip is moved, the stem slides into the opening 22. This can be proportioned to fit snugly over any standard fan stem and the clip thus held in place in a position substantially perpendicular to the axis of the fan stem. Motion of the air as induced by the fan can then cause that air to pick up the scent from the clip and spread the scent around the room.

Thus, the invention provides an air freshener adapted to different uses in a convenient inexpensive clip form.

I claim:

1. An air freshener for attachment to a fan stem having forced air flowed relative thereto and comprising:
   a scented clip formed from a flat sheet of polymeric material impregnated with a scented material, said sheet being perforated by a series of openings to allow air flow therethrough, said flat sheet being elongated and formed with legs defining a slot longitudinal of said elongation, said slot having a wider opening along said slot sized to engage said stem to hold such sheet in position on said stem for flow of said forced air through said openings.

2. An air freshener for mounting through a register vent including an array of louvers arranged to define on one side a working plane, said louvers being angled at a predetermined angle relative to said plane, said freshener comprising:
   a sheet of polymeric material formed with a planar section for laying along said array of louvers in said working plane and impregnated with scented material and formed with a series of air passage openings;
   said sheet further being formed with a handle including a transition neck projecting at said predetermined angle relative to said planar section for, when said section is positioned in said working plane, engaging a selected one of said louvers; and
   said handle being further formed with a tongue projecting therefrom and configured to, when said planar section is disposed in said working plane and said handle engaged with said selected one louver, engaging an adjacent louver to cooperate in holding said planar section positioned in said working plane.

3. An air freshener as set forth in claim 2 wherein:
   said section is elongated to, when said handle is engaged with said selected louver, project transversely of said louvers and said section is formed with an open ended slot to define spaced apart parallel legs.

4. An freshener as set forth in claim 3 wherein:
   said legs are resilient and are formed with confronting edges spaced apart a selected distance, at lest one of said edges being formed with a cut out defining an opening wider than said selected distance.

5. An air freshener as set forth in claim 2 wherein:
   said air passage openings are elongated.

6. An air freshener as set forth in claim 2 wherein:
   said sheet is flexible.

7. An air freshener as set forth in claim 2 wherein:
   said fragrance material forms between 15% and 25% of the weight of said section.

8. An air freshener as set forth in claim 2 wherein:
   said tongue projects at an acute angle relative to said neck.

9. An air freshener as set forth in claim 2 wherein:
   said neck projects at an angle of 60° from the plane of said section.

10. An air freshener as set forth in claim 2 wherein:
    said neck and tongue cooperate in forming a V-shape.

11. An air freshener as set forth in claim 2 wherein:
    said neck projects at an angle in one plane; and
    said handle projects at an obtuse angle relative to said one plane to define a finger grasp portion.

12. An air freshener as set forth in claim 2 wherein:
    said handle and planar section are integral.

13. An air freshener as set forth in claim 2 wherein:
    said planar section, handle and transition neck are one piece.

14. An air freshener as set forth in claim 2 wherein:
    said planar section, handle and tongue are integral.

15. An air freshener as set fort in claim 2 wherein:
    said handle and tongue are one-piece and are formed of polymeric material.

16. An air freshener as set forth in claim 2 wherein:
    said tongue is resilient.

17. An air freshener as set forth in claim 2 wherein:
    said neck is resilient.

18. An air freshener as set forth in claim 2 wherein:
    said working plane is on the interior side of said louvers and wherein, when said sheet is in said working plane, said transition neck angles outwardly along said one of said louvers.

19. An air freshener for insertion between adjacent louvers of an air vent and comprising:
    a planar sheet section of polymeric material for positioning in an installed position in a plane behind said vent, impregnated with scented material, and formed with a series of air passages; and
    mounting means including a transition neck, configured to be, when said sheet section is in said installed position in said plane behind said vent, angled outwardly along one of said adjacent louvers, and a tongue configured to angle from said neck to engage the other of said adjacent louvers and cooperate in holding said sheet section in said installed position.

20. An air freshener as set forth in claim 19 wherein:
    said planar sheet and mounting means are integral.

21. A louver mounted air freshener including:
    a sheet of polymeric material configured with a planar section disposed in a selected plane and impregnated with scented material and formed with a series of air passages spaced throughout;
    said sheet including a transition neck angling away from the plane of said planar sheet at an obtuse angle and configured on the distal extremity with a hand grasp section; and
    said hand grasp section including a tongue angling from said handle toward said plane and configured to project at an acute angle relative to said transition neck.

22. An air freshener as set forth in claim 1 wherein:
    said legs are integral.

23. An air freshener as set forth in claim 1 wherein:
    said legs are one piece.

24. An air freshener as set forth in claim 1 wherein:
    said clip is formed on one end with a handle.

25. A method of supplying air freshener to an enclosed area having a fixture mounted from a mounting stem disposed in a flow of moving air and including:
    selecting an air freshener constructed of an integral sheet of polymeric material impregnated with a scented material, having openings spaced throughout for flow of air thereinto, and formed with a pair of co-extensive resilient legs spaced apart to form an elongated open ended slot, at least one of the legs formed medially with a cut out confronting the other leg and configured such that it may be received over such stem; and
    mounting such freshener from said stem by inserting such legs over such stem to register it with said cut out to position said freshener in said air flow for flow of air into said openings to freshen the air in said enclosed area.

\* \* \* \* \*